United States Patent [19]

Johannisbauer et al.

[11] Patent Number: 5,710,261
[45] Date of Patent: Jan. 20, 1998

[54] PROCESS FOR THE SEPARATION OF ALCOHOLS BY DISTILLATION

[75] Inventors: Wilhelm Johannisbauer, Erkrath; Michael Nitsche, Solingen; Lutz Jeromin, Hilden, all of Germany

[73] Assignee: Henkel Kommanditgesellschaft auf Aktien, Duesseldorf, Germany

[21] Appl. No.: 594,506

[22] Filed: Jan. 31, 1996

Related U.S. Application Data

[63] Continuation of Ser. No. 318,850, filed as PCT/EP93/00929, Apr. 16, 1993, published as WO93/22323, Nov. 11, 1993, abandoned.

[30] Foreign Application Priority Data

Apr. 24, 1992 [DE] Germany ............... 42 13 456.0

[51] Int. Cl.$^6$ ................................................. O07H 15/04
[52] U.S. Cl. ............... 536/18.6; 536/124; 536/127; 203/89; 203/91; 159/49; 159/DIG. 10; 159/DIG. 16
[58] Field of Search ............... 536/18.6, 124, 536/127; 203/89, 91; 159/49, DIG. 10, DIG. 16

[56] References Cited

U.S. PATENT DOCUMENTS

| | | | |
|---|---|---|---|
| 4,611,055 | 9/1986 | Yamamoto et al. | 536/127 |
| 5,079,350 | 1/1992 | Fujita et al. | 536/124 |
| 5,138,046 | 8/1992 | Wuest et al. | 536/18.6 |
| 5,234,554 | 8/1993 | Muller et al. | 203/89 |
| 5,304,639 | 4/1994 | Gibson | 536/18.6 |

FOREIGN PATENT DOCUMENTS

| | | |
|---|---|---|
| 0032252 | 7/1981 | European Pat. Off. . |
| 0092876 | 11/1983 | European Pat. Off. . |
| 0092875 | 11/1983 | European Pat. Off. . |
| 0301298 | 2/1989 | European Pat. Off. . |
| 0377831 | 7/1990 | European Pat. Off. . |
| 0418458 | 3/1991 | European Pat. Off. . |
| 0421187 | 4/1991 | European Pat. Off. . |
| 3723826 | 1/1989 | Germany . |
| 3827534 | 2/1990 | Germany . |
| 3932173 | 4/1991 | Germany . |
| 9003977 | 4/1990 | WIPO . |
| WO91/04980 | 4/1991 | WIPO . |

*Primary Examiner*—John Kight
*Assistant Examiner*—Everett White
*Attorney, Agent, or Firm*—Wayne C. Jaeschke; John E. Drach; Steven J. Trzaska

[57] ABSTRACT

Aliphatic alcohols with up to 30 and especially with 6 to 18 carbon atoms are separated from a mixture of alkyl glycosides and alcohols which are unreacted during the production of these glycosides, by single or multi-stage distillation. The alcohols are distilled off by a drop film evaporator to impoverish the reaction mixture to residual alcohol contents of 5 wt % and under. The strip load of the drop film evaporator is set to at least 1.0 m$^3$/h m, especially at least 1.8 m$^3$/h m and preferably at least 3.0 m$^3$/h m. It is possible to reduce the alcohol content of the product to any value between 0.1 and 5 wt % at acceptable overall cost.

14 Claims, No Drawings

PROCESS FOR THE SEPARATION OF ALCOHOLS BY DISTILLATION

This application is a continuation of application Ser. No. 08/318,850, filed as PCT/EP93/00929 Apr. 16, 1993, published as WO93/22323 Nov. 11, 1993, now abandoned.

BACKGROUND OF THE INVENTION

This invention relates to a process for the single-stage or multistage separation of aliphatic alcohols containing up to 30 carbon atoms and, more particularly, 6 to 18 carbon atoms by distillation from a mixture of alkyl glycosides and alcohols remaining unreacted in the production of these alkyl glycosides.

STATEMENT OF RELATED ART

In the context of the invention, the term alkyl glycosides is used for the reaction products of sugars of any kind and aliphatic alcohols. The sugars may be mono-saccharides, such as pentoses and hexoses, disaccharides, such as sucrose and maltose, and polysaccharides, such as starch. The aldoses are preferred by virtue of their greater reactivity. Among the aldoses, glucose is preferred by virtue of its ready accessibility and availability in commercial quantities. The term alkyl in alkyl glycoside in its broadest sense applies to the residue of an aliphatic alcohol of any chain length, preferably a primary aliphatic alcohol and, more particularly, a fatty alcohol obtainable from natural fats, so that the term encompasses saturated and unsaturated residues and mixtures thereof, including those with various chain lengths in the mixture.

The carbohydrates are reacted with the alcohols in the presence of a suitable acidic catalyst. Mixtures of alkyl monoglycosides and alkyl polyglycosides or alkyl oligoglycosides are obtained. The terms alkyl oligoglycoside, alkyl polyglycoside, alkyl oligosaccharide and alkyl polysaccharide apply to those alkylated glycoses in which an alkyl group is attached in the form of the acetal to more than one glycose unit, i.e. to a polysaccharide or oligosaccharide unit. These terms are regarded as synonymous with one another. Accordingly, an alkyl monoglycoside is the acetal of a monosaccharide. Since mixtures are generally obtained in the acid-catalyzed reaction of sugars and fatty alcohols, the term alkyl glycoside used in the following encompasses both alkyl monoglycosides and alkyl poly(oligo)glycosides and, more particularly, mixtures thereof, including any secondary components, providing it is not specifically the structural differences which matter.

Alkyl glycosides can be produced on the one hand by the direct reaction of glycose, generally in the form of glucose, with an excess of the fatty alcohol and an acid as catalyst (direct synthesis) and, on the other hand, by the co-use of a lower alcohol or glycol as solvent and reactant (transacetalization). The reaction is generally carried out with a large excess of alcohol, so that a mixture of the alkyl glycosides and alcohols is obtained as the reaction product. To improve the performance properties of alkyl glycosides, the alcohols are normally removed from the mixture to a few % by weight or to less than 1% by weight. For economic reasons, the alcohols are then returned to the reactor.

One problem encountered in the production of surface-active alkyl glycosides based on typical fatty alcohols containing 12 to 18 carbon atoms lies in the difficulty of removing the unreacted part of the fatty alcohols from the reaction product by distillation. To this end, it is proposed in European patent application 32 252 to carry out the removal of these unreacted fatty alcohols by distillation in the presence of entraining agents, i.e. glycols of which the boiling points are at most 10° C. above or at most 30° C. below those of the alcohols to be removed. In this way, the distillation process can be carried out at no more than 140° C. and under a vacuum of around 8 mbar, i.e. under conditions which do not damage the product. Unfortunately, the addition of entraining agents has the disadvantage that the product comes into contact with additional substances which, on the one hand, can reduce the quality of the product and which, on the other hand, necessitate increased outlay on equipment for the removal and recycling of the entraining agent.

In another known process for the production of alkyl glycosides, transacetalization with a lower alcohol is carried out in an intermediate step. According to European patent application 92 875, the transacetalization process with butanol for the production of long-chain alkyl glucosides is controlled in such a way that the end product still contains a residue of butyl glucosides of less than 10% by weight. In this way, the formation of the long-chain alkyl oligoglucosides with a relatively high degree of oligomerization, i.e. with 6 and more glucose units in the molecule, is reduced. The products thus obtained consist essentially of alkyl monoglucoside and alkyl oligoglucosides, the alkyl monoglucosides making up at most 60% by weight and the average degree of oligomerization being from 1.5 to 3. The percentage content of short-chain alkyl glucosides, more particularly butyl glucosides, is below 10% while the percentage content of unreacted fatty alcohols is said to be below 2%. To remove the fatty alcohol by distillation, it is recommended to use a wiped film evaporator.

A general rule for the careful separation of temperature-sensitive mixtures is that falling film evaporators and, in particular, wiped film evaporators are particularly suitable for careful evaporation under reduced pressure because extremely short residence times at the relatively high temperatures required can be achieved in evaporators of this type. Wiped film evaporators are evaporators in which a highly viscous, high-boiling mixture is applied to a heated wall and is mechanically distributed thereon by rotating wiping elements. Thin, continuous liquid layers or liquid films are produced and the film surfaces are continuously renewed so that local overheating is avoided. The vapors formed flow against the product film and leave the evaporator in the externally arranged condenser. In wiped film evaporators, pressures of only a few mbar are applied and the residence time for the product is only a few seconds.

European patent application 92 876 also describes the production of long-chain alkyl glucosides with a degree of oligomerization of 1.5 to 20 by transacetalization with butanol, the catalyst (p-toluenesulfonic acid) responsible for transacetalization being inactivated by neutralization when at least 90% of the butyl glucoside has reacted, so that at most 10% of butyl glycoside still remains in the reaction product. In this case, too, it is recommended to use a wiped film evaporator for careful removal of the excess fatty alcohol. The presence of small quantities of butyl glycoside is important for reducing the viscosity of the mixture and hence for allowing relatively low temperatures. The reaction products are again said to contain less than 2% of free fatty alcohol.

In addition, to evaluate distillation-based separation processes, it is important that, so far as the exposure to heat is concerned, it is above all the residence time at the elevated temperature rather than the temperature itself which is crucial.

According to this prior art, the fatty alcohols can only be removed from the reaction mixture without thermal damage if alkyl glucosides with an alkyl radical of short chain length ($C_1$ to $C_5$) are present, i.e. only in the case of reaction mixtures obtained by the transacetalization route. Accordingly, the use of a wiped film evaporator for the removal of alcohols in the direct synthesis mentioned above leads to problems associated with the flowability of the reaction mixture and is not readily possible.

Another problem lies in the reduced operational reliability and useful life attributable to the moving parts of the wiped film evaporator.

A wiped film evaporator in which the liquid is mechanically distributed over the heating surface by wipers is also used in other known processes for the removal of fatty alcohol from the reaction mixture, at least in the final phase of the distillation process (EP 0 301 298 A1, WO 90/03977, WO 91/04980).

The problem addressed by the present invention was to improve the processes for removing the fatty alcohols. The process would also be applicable to reaction mixtures obtained by direct synthesis, could be carried out on an industrial scale in apparatus without any moving parts and, for reasonable overall costs, would reduce the alcohol content in the product to values of 0.1 to 5% by weight without adversely affecting the quality of the end product.

DESCRIPTION OF THE INVENTION

According to the invention, the solution to this problem is characterized in that the alcohols are removed with a falling film evaporator for stripping the reaction mixture to residual alcohol contents of 5% by weight or less, a linear load of the falling film evaporator of at least 3.0 $m^3$ feed per hour and per m circumferential length of the evaporator tubes being established. The linear load (also known as the "spezifischer Drucksatz") is the volume of liquid applied to the evaporator tubes per unit of time divided by the inner circumferential length which is obtainable from the product of the circumference of an individual tube and the number of evaporated tubes.

In falling-film evaporators, the liquid is distributed over the evaporator tubes from above by special fittings and flows downwards with the vapor formed into a separator for distillate and concentrate. The liquid normally runs down the inner walls of a number of vertical tubes heated from outside in the form of a continuous film. The development of a continuous film, which is uniform in all the tubes, requires the uniform distribution of the starting product over the tubes. The absence of mechanically moved parts increases the operational reliability of the falling film evaporator.

The required performance properties of the alkyl glycosides presuppose a residual alcohol content of less than about 5%, so that a highly viscous has to be processed, at least in the final phase of the distillation process. Although the use of wiped film evaporators is generally regarded as necessary for high-viscosity products such as these, which can only be exposed to an elevated temperature for short residence times, the alcohols can still surprisingly be removed in a falling film evaporator which, as well known, is intended more for products of relatively low viscosity which, in addition, allow longer residence times.

Under normal process conditions, however, a wiped film evaporator could not be replaced by a falling film evaporator without a distinct deterioration in the quality of the end product. This is because the high viscosity of the mixture towards the end of the distillation process complicates the formation of a uniform liquid film over the entire heat-exchange surface of the evaporator tubes, particularly towards the lower end of the tubes. Unwetted parts of the tube wall and, hence, local overheating and thermal damage to the product would occur, giving rise to colored impurities and secondary products. Serious caking would also occur, causing a reduction in the cross-section of the tubes and, ultimately, blockage of the tubes.

According to the invention, these difficulties are avoided by a certain flow pattern in the falling film evaporator which provides for complete wetting of the heat-exchange surfaces with a uniform liquid film, even at the lower end of the evaporator tubes, so that local overheating through cracks in the liquid film is avoided. This requirement can be satisfied—despite the high viscosity—by the high minimum value mentioned above for the linear load.

However, linear loads of less than 1 $m^3$/h m are normally applied for high evaporation ratios, i.e. for a large amount of distillate to be separated, so that the heat transferable to the heating surface is sufficient for removing all the low-boiling fractions.

The invention is based on the following observation. In the processing of temperature-sensitive mixtures in a falling film evaporator, a very thin film and a short residence time are required to minimize exposure to heat. However, during the separation of the alcohols from the alkyl glycosides, the viscosities and hence the flow conditions change considerably over the length of the tubes, so that it is relatively difficult to guarantee complete wetting of the heat exchange surfaces. Now, the invention is based on a balanced consideration of the factors responsible for exposure to high temperatures. Local overheating caused by cracks in the film is far more responsible for heat damage than a relatively high layer thickness or a relatively long residence time which are accepted in accordance with the present invention. Accordingly, the formation—whatever the conditions—of a continuous liquid film with no cracks or unwetted areas by careful adherence to the minimum linear load mentioned is crucial to the invention.

The process according to the invention can be operated particularly economically if it is carried out in several stages, more particularly two stages, and if a falling film evaporator is used as the evaporator unit in each stage. The reaction mixture is preferably reduced to an alcohol content of 5 to 50% by weight and, more particularly, 10 to 30% by weight in the preliminary stages. Alcohol contents of less than 10% by weight are reached in the last stage.

However, the process according to the invention may also be carried out in a single stage. Depending on the construction of the falling film evaporator used for the last distillation stage, the process according to the invention may be carried out by mainly two variants of which each affords particular advantages for different objectives.

The single-stage process may be carried out by a single passage of the reaction mixture through the evaporator tubes. The large amount of distillate to be removed in only one stage requires relatively long evaporator tubes to obtain a concentrate having the maximum residual alcohol content required. The considerable length of the tubes and, in particular, the significant change in the composition and viscosity of the liquid and hence in the flow conditions along the tube require a relatively thick liquid film and an unusually high linear load of at least 3.0 $m^3$/h m. The short residence time attributable to the single passage through the tube and, hence, the minimal exposure to heat are advantages in this regard.

Another embodiment of the single-stage process uses forced external circulation. The mixture to be worked up is circulated by a circulation pump arranged outside the falling film evaporator. A small quantity of crude product by comparison with the circulation rate is introduced into the circuit while a corresponding amount of concentrated product is removed therefrom. The multiple circulation of the liquid provides for shorter tube lengths by comparison with the single passage variant and hence for a more compact construction of the plant or for a higher throughput in a plant of the same size. The composition of the liquid mixture changes less over the length of the tubes and the more uniform flow conditions provide for a thinner film and a lower linear load of at least 1.0 m$^3$/h m for a ratio of feed to circulation rate of 1:100 to 1:5. In this case, the linear load is calculated from the total volume of liquid delivered to the evaporator, i.e. the circulated volume. Despite the smaller film thickness, complete wetting of the tube wall with the liquid applied remains guaranteed over the entire length of the tube.

Accordingly, depending on the throughput required and on the temperature sensitivity of the product, it is of advantage to carry out single-stage distillation either with or without forced external circulation.

Particularly preferred pressures and temperatures for operating the process according to the invention are mentioned in the following.

In multistage processes, a sump temperature of 100° to 220° C. and, more particularly, 140° to 200° C. and an operating pressure of 0.5 to 20 mbar and, more particularly, 1 to 10 mbar are established for the stages preceding the last evaporator stage.

Single-stage processes and the last evaporator stage of multistage processes are advantageously carried out with sump temperatures of 120° to 250° C. and, more particularly, 160° to 230° C. and under operating pressures of 0.1 to 10 mbar and, more particularly, 0.5 to 5 mbar.

After removal of the excess fatty alcohol, the end reaction product, which forms a light brown wax-like mass after cooling, the final reaction product is preferably converted into a water-containing paste with an active substance content of around 60% in the interests of better handling. Where the colorlessness of the end product has to meet stringent requirements, bleaching with hydrogen peroxide or an organic peracid, such as dodecane diperacid for example, may be carried out during or after production of the water-containing paste.

The following Examples are intended to illustrate the invention without limiting it in any way.

EXAMPLES

Example 1
Two-stage distillation with liquid circulation

A mixture of alkyl glycosides (APG) and fatty alcohols was separated in a two-stage distillation plant consisting of a first falling film evaporator with an evaporator area of 2.5 m$^2$ and a second, following falling film evaporator with an evaporator area of 4.5 m$^2$. The alkyl glucosides had been synthesized from glucose sirup and a mixture of lauric and myristic alcohol, the molar ratio of glycose to alcohol being 1:4.9.

The first falling film evaporator was operated at a heating medium temperature of 180° C., a sump temperature of 160° C. and a pressure of around 2 mbar. The second falling film evaporator was operated at a heating medium temperature of 210° C., a sump temperature of 200° C. and a pressure of around 2 mbar.

In the first distillation stage, the fatty alcohol content was reduced to around 10% by weight. The introduction of liquid and the uniform wetting of the tube walls in the first evaporation stage, in which a relatively large amount of distillate accumulated, were facilitated by forced external circulation. In the steady operating state, 4.0 m$^3$/h were circulated. 0.3 m$^3$/h were fed in. In this case, the linear load was 4.8 m$^3$/h m.

In the second distillation stage, 0.12 m$^3$/h were fed in from the first stage and 5.0 m$^3$/h were circulated in the steady state. The second distillation stage was also operated with forced external circulation. The linear load was 3.0 m$^3$/h m. The fatty alcohol content was reduced to 0.7% by weight.

A light brown mass was obtained and, after conversion into an aqueous paste containing around 60% of APG, could be bleached to form a light yellow to almost colorless product. The product was alkali-stable.

Example 2
Single-stage distillation with liquid circulation

The test was carried out as in Example 1, but with single-stage evaporation in a falling film evaporator with an evaporator area of 2.5 m$^2$ at a feed rate of 0.05 m$^3$/h, a heating medium temperature of 210° C., a sump temperature of 200° C. and a pressure of around 2 mbar. The distillation plant was operated with forced external circulation, 4.0 m$^3$/h being circulated. The linear load was 4.8 m$^3$/h m.

The light brown mass obtained had a fatty alcohol content of 0.8% by weight. The corresponding aqueous paste with an APG content of 60% bleached with hydrogen peroxide was light yellow to almost colorless.

Example 3
Single-stage distillation with liquid circulation

A single-stage distillation with forced external circulation was carried out in the same distillation plant as in Example 2 with a feed rate of 0.05 m$^3$/h and a circulation rate of 4.0 m$^3$/h. An alkyl polyglucoside based on glucose and a mixture of capryl and capric alcohol was used, the molar ratio of glucose and alcohol in the reaction being 1:2.5. The distillation plant was operated at a heating medium temperature of 180° C., a sump temperature of 170° C., a pressure of 2 mbar and a linear load of 4.8 m$^3$/h m.

The fatty alcohol content of the concentrate was 0.5% by weight. The product converted into an aqueous paste containing around 70% of APG and bleached with hydrogen peroxide was light yellow to almost colorless.

Example 4
(Comparison Example)

Same conditions as in Example 2, i.e. an evaporator area of 2.5 m$^2$, a feed rate of 0.05 m$^3$/h, a heating medium temperature of 210° C. and a pressure of 2 mbar were established.

The reduction in the circulation rate from 4.0 m$^3$/h (corresponding to a linear load of 4.8 m$^3$/h m) to 0.6 m$^3$/h (linear load including feed rate 0.78 m$^3$/h m) led to a dark brown product with a fatty alcohol content of 2.5 to 4% by weight.

A further reduction in the circulation rate to 0.3 m$^3$/h (linear load including feed rate 0.42 m$^3$/h m) led to a dark brown to black product with a fatty alcohol content of 4 to 5% by weight.

We claim:

1. A process for reducing the aliphatic alcohol content of a mixture comprised of an alkyl polyglycoside and an aliphatic alcohol having up to about 30 carbon atoms comprising passing a mixture comprised of an alkyl polyglycoside and one or more aliphatic alcohols having up to about 30 carbon atoms through a falling film evaporator wherein the linear load in said evaporator is at least 1.0 m³/h m.

2. The process of claim 1 wherein said linear load is at least 3.0 m³/h m.

3. The process of claim 1 wherein the aliphatic alcohol content is reduced to a value of from about 50% to about 5% by weight.

4. The process of claim 1 wherein the aliphatic alcohol content is reduced to a value of from about 30% to about 10% by weight.

5. The process of claim 1 wherein said falling film evaporator is a forced circulation evaporator.

6. The process of claim 5 wherein the ratio of feed to circulating liquid is from about 100:1 to about 1:5 and said linear load is at least 1.0 m³/h m.

7. A multi-stage process for reducing the aliphatic alcohol content of a mixture comprised of an alkyl polyglycoside and an aliphatic alcohol having up to about 30 carbon atoms comprising passing a mixture comprised of an alkyl polyglycoside and one or more aliphatic alcohols having up to about 30 carbon atoms through a first falling film evaporator and then passing the output of said first evaporator through one or more additional falling film evaporators arranged serially wherein the linear load in each of said evaporators is at least 1.0 m³/h m.

8. The process of claim 7 wherein said linear load in each of said evaporators is at least 3.0 m³/h m.

9. The process of claim 7 wherein the aliphatic alcohol content is reduced to a value of from about 50% to about 5% by weight.

10. The process of claim 9 wherein the aliphatic alcohol content is reduced to a value of from about 30% to about 10% by weight.

11. The process of claim 7 wherein the stages preceding the last stage are operated at a sump temperature of from about 100° C. to about 220° C. and a pressure of from about 0.5 mbar to about 20 mbar.

12. The process of claim 11 wherein said sump temperature is from about 140° C. to about 200° and said pressure is from about 1 mbar to about 10 mbar.

13. The process of claim 7 wherein the last stage is operated at a sump temperature of from about 120° C. to about 250° C. and a pressure of from about 0.1 mbar to about 10 mbar.

14. The process of claim 12 wherein said sump temperature is from about 160° C. to about 230° and said pressure is from about 0.5 mbar to about 5 mbar.

* * * * *